(12) United States Patent
Freeman et al.

(10) Patent No.: US 10,640,471 B2
(45) Date of Patent: *May 5, 2020

(54) FORMATION OF N-PROTECTED 3,6-BIS-(4-AMINOALKYL)-2,5, DIKETOPIPERAZINE

(71) Applicant: MannKind Corp, Valencia, CA (US)

(72) Inventors: John J. Freeman, New Fairfield, CT (US); Adrienne Stamper, Naugatuck, CT (US); Melissa Heitmann, Hopewell Junction, NY (US)

(73) Assignee: MANNKIND, CORP., Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/266,683

(22) Filed: Feb. 4, 2019

(65) Prior Publication Data

US 2019/0169135 A1 Jun. 6, 2019

Related U.S. Application Data

(63) Continuation of application No. 15/237,427, filed on Aug. 15, 2016, now Pat. No. 10,196,366, which is a continuation of application No. 14/543,464, filed on Nov. 17, 2014, now Pat. No. 9,416,113, which is a continuation of application No. 13/368,172, filed on Feb. 7, 2012, now Pat. No. 8,912,328.

(60) Provisional application No. 61/441,525, filed on Feb. 10, 2011.

(51) Int. Cl.
    C07D 241/08 (2006.01)
    B01J 31/02 (2006.01)

(52) U.S. Cl.
    CPC ........ *C07D 241/08* (2013.01); *B01J 31/0225* (2013.01); *B01J 31/0258* (2013.01); *B01J 31/0259* (2013.01); *B01J 2231/40* (2013.01)

(58) Field of Classification Search
    CPC .................................................. C07D 241/08
    See application file for complete search history.

(56) References Cited

U.S. PATENT DOCUMENTS

| 5,352,461 | A | 10/1994 | Feldstein |
| 2004/0024180 | A1 | 2/2004 | Drauz |
| 2006/0041133 | A1 | 2/2006 | Stevenson et al. |

FOREIGN PATENT DOCUMENTS

| WO | 2001/081321 | 11/2001 | |
| WO | 2006/023849 | 3/2006 | |
| WO | WO-2006023849 A2 * | 3/2006 | ........... C07D 241/08 |

OTHER PUBLICATIONS

International Search Report from PCT/US2012/024160 dated Aug. 10, 2012.
Office Action from U.S. Appl. No. 13/368,172 dated Apr. 12, 2013.
Final Office Action from U.S. Appl. No. 13/368,172 dated Oct. 25, 2013.
Office Action from U.S. Appl. No. 13/368,172 dated Jan. 15, 2014.
Notice of Allowance from U.S. Appl. No. 13/368,172 dated Aug. 7, 2014.
Office Action from U.S. Appl. No. 14/543,464 dated Jun. 25, 2015.
Ex Parte Quayle Action from U.S. Appl. No. 14/543,464 dated Jan. 14, 2016.
Notice of Allowance from U.S. Appl. No. 14/543,464 dated Apr. 14, 2016.
Examination and Search Report from AE 851/2013 dated Feb. 11, 2018.
Office Action from CA 2826973 dated Jan. 18, 2018.
First Office Action from CN 201280008649.7 dated Oct. 6, 2013.
Second Office Action from CN 201280008649.7 dated Dec. 22, 2014.
Third Office Action from CN 201280008649.7 dated Jul. 14, 2015.
First Office Action from CN 201610169104.4 dated Nov. 3, 2017.
Search Report for EP 12744320 dated Aug. 1, 2014.
First Office Action in IL 227904 dated Jun. 28, 2015.
Examination Report for IN 7714/DELNP/2013 dated Feb. 2, 2018.
First Office Action from SG 2013060793 dated Jul. 21, 2014.
Second Office Action from SG 2013060793 dated Jan. 5, 2015.
Kaur et al., Molecular Pharmaceutics vol. 5, No. 2, 294-315, published Feb. 7, 2008.
Jass et al., "Use of N-trifluoroacetyl-protected amino acid chlorides in peptide couplingreactions with virtually complete preservation of stereochemistry," Tetrahedron vol. 59, No. 45, Nov. 3, 2003, pp. 9019-9029.
Office Action from U.S. Appl. No. 15/237,427 dated Jan. 23, 2017.
Office Action from U.S. Appl. No. 15/237,427 dated Oct. 4, 2017.

(Continued)

*Primary Examiner* — Noble E Jarrell
*Assistant Examiner* — John S Kenyon
(74) *Attorney, Agent, or Firm* — Callee, Halter & Griswold LLP

(57) ABSTRACT

The disclosed embodiments detail improved methods for the synthesis of diketopiperazines from amino acids. In particular improved methods for the cyclocondensation and purification of N-protected 3,6-(aminoalkyl)-2,5-diketopiperazines from N-protected amino acids. Disclosed embodiments describe methods for the synthesis of 3,6-bis-[N-protected am inoalkyl]-2,5-diketopiperazine comprising heating a mixture of an amino acid in the presence of a catalyst in an organic solvent. The catalyst is selected from the group comprising sulfuric acid, phosphoric acid, p-toluenesulfonic acid, 1-propylphosphonic acid cyclic anhydride, tributyl phosphate, phenyl phosphonic acid and phosphorous pentoxide among others. The solvent is selected from the group comprising: dimethylacetamide, N-methyl-2-pyrrolidone, diglyme, ethyl glyme, proglyme, ethyldiglyme, m-cresol, p-cresol, o-cresol, xylenes, ethylene glycol and phenol among others.

19 Claims, 1 Drawing Sheet

(56) References Cited

OTHER PUBLICATIONS

Notice of Allowance from U.S. Appl. No. 15/237,427 dated Apr. 3, 2018.
Notice of Allowance from U.S. Appl. No. 15/237,427 dated Oct. 4, 2018.
Office Action from CA 2826973 dated Oct. 4, 2018.
Notice of Acceptance from AE 851/2013 dated Sep. 30, 2018.
Office Action from CN 201610169104.4 dated Aug. 1, 2018.
Office Action from AU 2017203860 dated Feb. 8, 2019.
Publication Notification for SG 10201802008T dated Apr. 27, 2018.

* cited by examiner

FORMATION OF N-PROTECTED 3,6-BIS-(4-AMINOALKYL)-2,5, DIKETOPIPERAZINE

CROSS-REFERENCE TO RELATED APPLICATIONS

This application is a continuation of U.S. Non-provisional application Ser. No. 15/237,427, now U.S. Pat. No. 10,196,366, filed Aug. 15, 2016, which is a continuation of U.S. Non-provisional application Ser. No. 14/543,464, now U.S. Pat. No. 9,416,113, filed Nov. 17, 2014, which is a continuation of U.S. Non-provisional application Ser. No. 13/368,172, now U.S. Pat. No. 8,912,328, filed Feb. 7, 2012, which, in turn, claims the benefit of U.S. Provisional Application No. 61/441,525 filed on 10 Feb. 2011, the content of which are hereby incorporated by reference as if fully recited herein.

TECHNICAL FIELD

The present invention relates to compositions for delivering active agents, and particularly biologically active agents. Disclosed embodiments are in the field of chemical synthesis and more particularly are related to improved synthetic methods for the preparation and purification of 3,6-di-substituted-2,5-diketopiperazines.

BACKGROUND

Drug delivery is a persistent problem in the administration of active agents to patients. Conventional means for delivering active agents are often severely limited by biological, chemical, and physical barriers. Typically, these barriers are imposed by the environment through which delivery occurs, the environment of the target for delivery, or the target itself.

Biologically active agents are particularly vulnerable to such barriers. For example, in the delivery of pharmacological and therapeutic agents to humans, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically active agents would be the route of choice for administration to animals if not for biological, chemical, and physical barriers such as varying pH in the gastrointestinal (GI) tract, powerful digestive enzymes, and active agent impermeable gastrointestinal membranes. Among the numerous agents which are not typically amenable to oral administration are biologically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastrointestinal tract by acid hydrolysis, enzymes, or the like.

However, broad spectrum use of drug delivery systems is often precluded because: (1) the systems require toxic amounts of adjuvants or inhibitors; (2) suitable low molecular weight active agents are not available; (3) the systems exhibit poor stability and inadequate shelf life; (4) the systems are difficult to manufacture; (5) the systems fail to protect the active agent; (6) the systems adversely alter the active agent; or (7) the systems fail to allow or promote absorption of the active agent.

There is still a need in the art for simple, inexpensive delivery systems which are easily prepared and which can deliver a broad range of active agents. One class of delivery system that has shown promise as excipients is diketopiperazines (DKP). In particular, 3,6-bis-substituted-2,5-diketopiperazines have been shown to effectively deliver biologically active agents across the lining of the lung.

Conventional synthesis of diketopiperazines proceeds via a cyclocondensation of two amino acid molecules or a dipeptide. One exemplary process for the synthesis of diketopiperazines, entails heating an amino acid (Cbz-L-lysine for example) in m-cresol for between 17 and 22 hours at 160-170° C., and recrystallizing the diketopiperazine from acetic acid for a yield of about 48%.

U.S. Pat. No. 7,709,639 to Stevenson et. al. details methods for the synthesis of bis-Cbz-N-protected diketopiperazines, the disclosure of which is hereby incorporated by reference in its entirety as if recited fully herein.

Others have generated diketopiperazines from isolated dipetides by heating in an appropriate solvent while removing water by distillation. While these provide the desired diketopiperazines, the methods provide suboptimal yields and may require prolonged purification. Thus, there is a need for an improved method for the synthesis of disubstituted 2,5-diketopiperazines that provides the N-protected diketopiperazines in good yield while preserving the protecting groups and requiring minimal purification.

SUMMARY

This and other unmet needs of the prior art are met by compounds and methods as described in more detail below. The use of N-substituted 3,6-aminoalkyl-2,5-diketopiperazines as pharmaceutical excipients has shown considerable promise. As noted above, these compounds are often synthesized via cyclocondensation of amino acids. If the amino acid has a free nitrogen on its side-chain (as in, for example, lysine or ornithine) it is often necessary to have this nitrogen blocked prior to the cyclization reaction. Because of the potential for disparate synthetic processes after cyclization, compatibility with a variety of protecting groups is desired. Thus a synthetic method that can accommodate a number of diverse N-protecting groups and produce good yield of N-protected diketopiperazine is desired.

Some useful protecting groups include trifluoroacteyl, acetyl and other amide forming protecting groups; carbamate protecting groups including benzyloxycarbonyl (Cbz) and t-butoxycarbonyl (BOC).

In an embodiment, 3,6-bis-4-(N-trifluoroacetyl)aminobutyl-2,5-diketopiperazine is formed by heating ε-trifluoroacetyl-L-lysine in a water miscible solvent such as N-methyl-2-pyrrolidone (NMP) in the presence of a catalyst chosen from the group comprising phosphoric acid, sulfuric acid and phosphorous pentoxide to a temperature of about 150-175° C. The diketopiperazine is isolated by quenching with water and filtering the resulting solid.

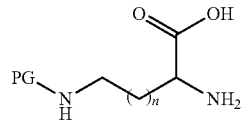

Formula I

Disclosed embodiments describe methods for the synthesis of 3,6-bis-[N-protected aminoalkyl]-2,5-diketopiperazine comprising heating a mixture of an amino acid of general formula I in the presence of a catalyst in an organic solvent; wherein the catalyst is selected from the group comprising sulfuric acid, phosphoric acid, p-toluenesulfonic acid, 1-propylphosphonic acid cyclic anhydride, tributyl phosphate, phenyl phosphonic acid and phosphorous pentoxide among others; and wherein the solvent is selected from the group comprising: dimethylacetamide, N-methyl-2-pyrrolidone, diglyme, ethyl glyme, proglyme, ethyldiglyme, m-cresol, p-cresol, o-cresol, xylenes, ethylene glycol and phenol among others.

The disclosed embodiments also describe methods wherein n is between from 1 to 7, wherein n is equal to 3, wherein n is equal to 2, wherein PG is an amide forming protecting group, wherein the protecting group is trifluoroacetyl, wherein PG is a carbamate forming protecting group, wherein the protecting group is Cbz, wherein the solvent is substantially water miscible, wherein the solvent is N-methyl-2-pyrrolidone, wherein the amino acid is ε-trifluoroacetyl-L-lysine, wherein the amino acid is ε-Cbz-L-lysine, wherein the amino acid is γ-trifluoroacetyl-ornithine, wherein the amino acid is γ-Cbz-ornithine, wherein the catalyst is phosphorous pentoxide, wherein the concentration of phosphorous pentoxide is from 10% to about 50% that of the amino acid, and embodiments further comprising the step of quenching the mixture with water.

Disclosed embodiments describe methods for the synthesis of 3,6-bis-[N-protected aminobutyl]-2,5-diketopiperazine comprising: heating a mixture of a N-protected lysine in the presence of a catalyst in an organic solvent, to a temperature of between 110° and 175° C. for between 0.25 and 5 hours; wherein the catalyst is selected from the group comprising sulfuric acid, phosphoric acid and phosphorous pentoxide, the concentration of catalyst from about 5% to about 50% that of the lysine; and the solvent is selected from the group comprising: dimethylacetamide, N-methyl-2-pyrrolidone, diglyme, ethyl glyme, proglyme, ethyldiglyme, m-cresol, p-cresol, o-cresol, xylenes, ethylene glycol and phenol.

Disclosed embodiments describe methods for the synthesis of 3,6-bis-4-(N-trifluoroacetyl)aminobutyl-2,5-diketopiperazine comprising: heating a mixture of ε-trifluoroacetyl-L-lysine in the presence of phosphorous pentoxide in N-methyl-2-pyrrolidone, to a temperature of between 150° and 175° C. for between 0.25 and 5 hours, the concentration of phosphorous pentoxide is from about 10% to about 40% that of the lysine; and quenching the mixture with a second solvent, or alternatively, wherein the concentration of phosphorous pentoxide to lysine is between 20% and 35% and the mixture is quenched with water.

Any combination of the above described elements in all possible variations thereof is encompassed by the disclosed embodiments unless otherwise indicated herein or otherwise clearly contradicted by context.

BRIEF DESCRIPTION OF THE DRAWINGS

A better understanding of the exemplary embodiments of the invention will be had when reference is made to the accompanying drawings, wherein identical parts are identified with identical reference numerals, and wherein.

DETAILED DESCRIPTION

As used herein, methyl, ethyl, n-propyl, isopropyl, n-butyl, isobutyl, sec-butyl, tert-butyl, pentyl, hexyl, heptyl or octyl and all bond isomers are to be considered as alkyl. These can be mono- or poly-substituted with (C1-C8)-alkoxy, (C1-C8)-haloalkyl, OH, halogen, $NH_2$, $NO_2$, SH, S—(C1-C8) alkyl. (C2-C8)-alkenyl, with the exception of methyl, is understood to mean a (C1-C8)-alkyl group as illustrated above having at least one double bond.

A side-chain group of an α-amino acid is understood to mean the changeable group on the α-C atom of glycine as the basic amino acid. Natural amino acids are given for example in Bayer-Walter, Lehrbuch der organischen Chemie, S. Hirzel Verlag, Stuttgart, 22nd edition, page 822ff. Preferred synthetic amino acids and protected amino acids are available from the Sigma-Aldrich Company. The side chain groups can be derived from those referred to there.

The stated chemical structures relate to all possible stereoisomers that can be obtained by varying the configuration of the individual chiral centers, axes or surfaces, in other words all possible diastereomers as well as all optical isomers (enantiomers) falling within this group.

Figure 1:
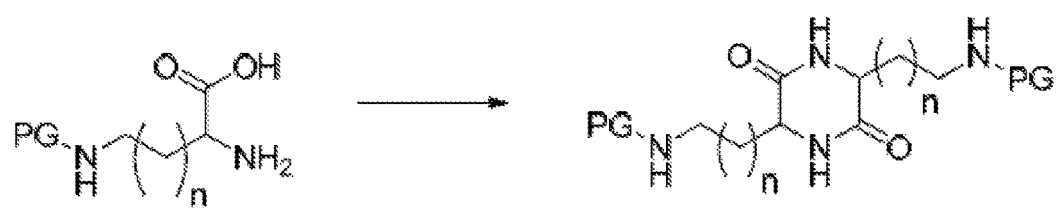
FIG. 1 is a scheme showing the cyclocondensation of an N-protected amino acid into a diketopiperazine.

Turning to the drawings for a better understanding, FIG. 1 shows a general scheme for the synthesis of a disubstituted diketopiperazine. This scheme shows an N-protected amino acid undergoing a cyclocondensation with a second amino acid molecule. In this embodiment, PG represents a protecting group for the nitrogen and n may be from 0 to 7. It is evident from the scheme that it is necessary when forming a diketopiperazine with an amine on a side chain that the nitrogen(s) must be blocked prior to the cyclization reaction or yields will be affected by unwanted side condensations. Depending on the chemistry that will be performed after ring formation, a variety of protecting groups are desired, and thus a method that accommodates many groups is preferred. Some useful protecting groups include trifluoroacteyl, acetyl and other amide forming protecting groups; carbamate protecting groups including benzyloxycarbonyl (Cbz) and t-butoxycarbonyl (BOC).

Known methods of cyclocondensation of amino acids to form DKP employed solvents such as n-butanol (water miscibility of about 7-8%), whereas solvents such as NMP are more miscible with water allowing a simple water quench/wash to remove reaction solvent and, if the catalyst has significant water solubility, the catalyst, all at once. In an embodiment, the catalyst for the amino acid cyclocondensation is water soluble allowing a water quench and subsequent removal by filtration.

Figure 2:
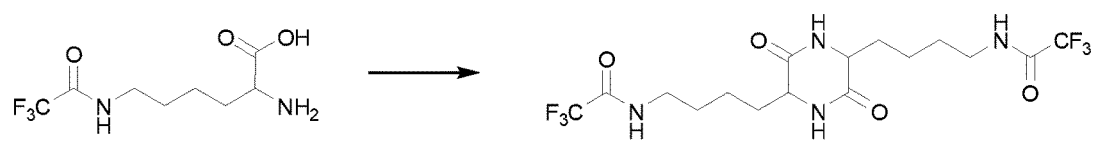
FIG. 2 is a scheme showing the cyclocondensation of ε-trifluoroacetyl lysine.

FIG. 2 illustrates an embodiment wherein PG is trifluoroacetyl and n is equal to 3. Thus, the starting amino acid is ε-trifluoroacetyl lysine and the product is 3,6-bis-4-(N-trifluoroacetyl)aminobutyl-2,5-diketopiperazine. An example of a method for the synthesis of 3,6-bis-4-(N-trifluoroacetyl)aminobutyl-2,5-diketopiperazine follows:

EXAMPLES

Example 1 and 2

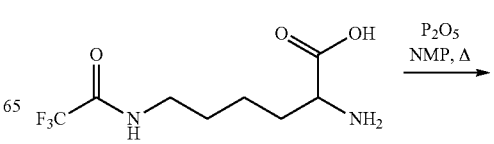

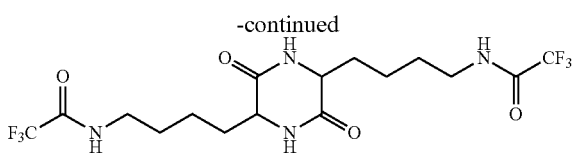

To a 1 L, 3-neck round bottom flask equipped with a nitrogen purge, a distillation apparatus, a mechanical stirrer and a thermocouple with a temperature display, was added: NMP (256 mL), TFA-Lys (125 g, 0.52 mol) and P2O5 (22 g, 0.15 mol). The reaction mixture was heated to 160° C. and held there for 1.5 h. The mixture was then cooled to 100° C. and poured into DI water. The mixture was then cooled below 25° C. and the solids were isolated via filtration, washed with DI water and dried in vacuo at 50° C. to yield 3,6-bis-4-(N-trifluoroacetyl)aminobutyl-2,5-diketopiperazine (65.28 g, 56.4%). $^1$H-NMR (DMSO-$d_6$): 1.3 (m, 4H), 1.5 (m, 4H), 1.7 (m, 4H), 3.2 (q, 4H), 3.8 (m, 2H), 8.1 (s, 2H), 9.4 (s, 2H). Elemental analysis, calc'd C: 42.86; H: 4.95; N, 12.50; F: 25.42. Found: C: 42.95; H: 4.91; N: 12.53; F: 24.99.

To a 100 gallon glass-lined reactor was added N-methyl-2-pyrollidone (200 L) and stirring was started. To the solvent was added TFA-lysine (100 kg, 413 mol) at ambient temperature. To the resulting slurry was added phosphorous pentoxide (15.2 kg, 107 mol). The mixture was then heated to 160° C. for 1 h. After 1 h at 160° C. the mixture was cooled to 100° C. and water (500 L) was added. The resulting mixture was cooled to 25° C. and held there for 90 minutes. The resulting solids were washed twice with water (265 L each) and isolated by filtration to give 3,6-bis-4-(N-trifluoroacetyl)aminobutyl-2,5-diketopiperazine in 50% yield.

A variety of catalysts were examined for the formation of bis-substituted diketopiperazines. The results of the catalyst survey are shown in Table 1. A general scheme and example for this survey follows:

Example 3

Cbz-lysine (10.0 g), diethylene glycol dimethyl ether (diglyme; 50 mL), and a catalyst were charged to a 250 mL round bottom flask. The mixture was heated to 160-165° C. for 2.5 hours. The reaction mixture was poured into water and cooled to ambient temperature overnight. The precipitated solid was isolated by filtration, washed with water, and dried in vacuo at 50° C.

TABLE 1

Catalysts for diketopiperazine synthesis.

| Catalyst | Amount | Reaction yield |
|---|---|---|
| P$_2$O$_5$ | 0.76 g (0.15 eq.) | 55% |
| P$_2$O$_5$ | 1.76 g (0.30 eq.) | 45% |
| H$_2$SO$_4$ | 1.27 mL (0.35 eq.) | 55% |
| H$_3$PO$_4$ | 0.73 mL (0.30 eq.) | 65% |
| p-toluene sulfonic acid | 3.39 g (0.50 eq.) | 52% |
| 1-propylphosphonic acid cyclic anhydride | 4.54 g (0.20 eq.) | 79% |
| tributyl phosphate | 2.44 g (0.30 eq.) | 89% |
| ethyl phosphonic acid | 1.18 g (0.30 eq.) | 0% |
| phenyl phosphonic acid | 1.13 g (0.20 eq.) | 78% |

Sulfuric acid and phosphorous pentoxide (at two concentrations) were surveyed further for synthesis of 3,6-bis-4-(N-trifluoroacetyl)aminobutyl-2,5-diketopiperazine in diglyme. The results are shown in Table 2.

Example 4

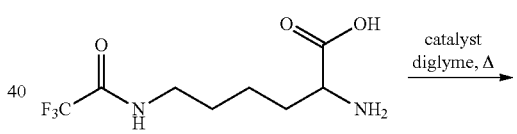

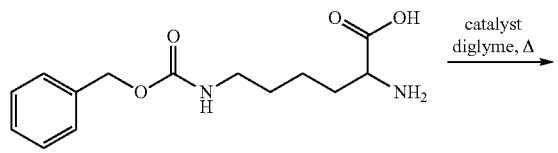

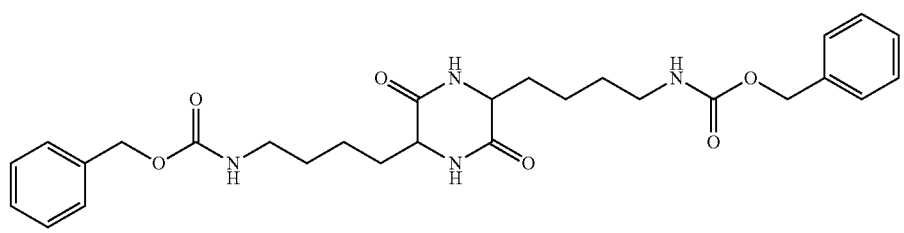

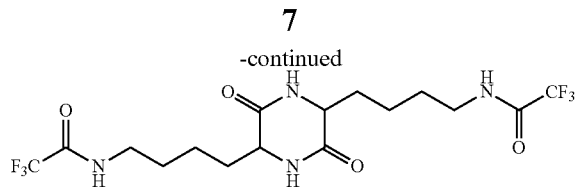

TFA-lysine (10.0 g), diethylene glycol dimethyl ether (50 mL), and a catalyst were charged to a 250 mL round bottom flask. The mixture was heated to 160-165° C. for 2.5 hours. The reaction mixture was poured into water and cooled to ambient temperature. The precipitated solid was isolated by filtration, washed with water and dried in vacuo at 50° C.

TABLE 2

Catalysts for TFA-lysine diketopiperazine synthesis.

| Catalyst | Amount | Reaction yield |
|---|---|---|
| $P_2O_5$ | 0.88 g (0.15 eq.) | 41% |
| $P_2O_5$ | 1.76 g (0.30 eq.) | 55% |
| $H_2SO_4$ | 0.8 mL (0.35 eq.) | 40% |

Sulfuric acid and phosphorous pentoxide (at two concentrations) were surveyed further for synthesis of 3,6-bis-4-(N-trifluoroacetyl)aminobutyl-2,5-diketopiperazine in dimethylacetamide (DMAc). The results are shown in Table 3.

Example 5

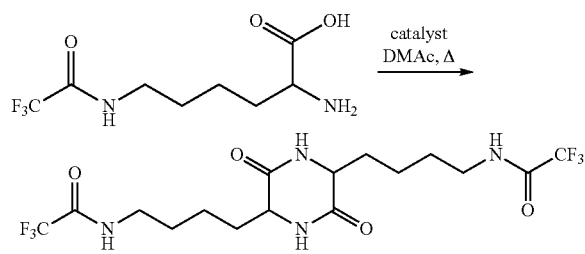

TFA-lysine (25.0 g), dimethylacetamide (125 mL), and a catalyst were charged to a 250 mL round bottom flask. The mixture was heated to 160-165° C. for 2.5 hours. The reaction mixture was cooled to 100° C., poured into water, and then cooled to ambient temperature. The precipitated solid was isolated by filtration, washed with water and dried in vacuo at 50° C. The results are shown in Table 3.

TABLE 3

Catalysts for TFA-lysine diketopiperazine synthesis.

| Catalyst | Amount | Reaction yield |
|---|---|---|
| $P_2O_5$ | 2.2 g (0.15 eq.) | 35% |
| $P_2O_5$ | 5.13 g (0.35 eq.) | 50% |
| $H_2SO_4$ | 4.19 g (0.40 eq.) | 16% |

The use of phosphorous pentoxide was examined for the synthesis of 3,6-bis-4-(N-trifluoroacetyl)aminobutyl-2,5-diketopiperazine in N-methyl-2-pyrrolidone (NMP) at different times and temperatures. The results are shown in Table 4.

Example 6

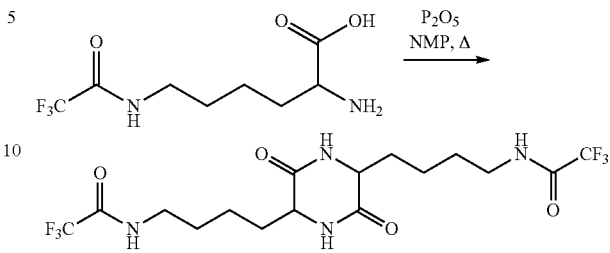

TFA-lysine (50 g), N-methyl pyrrolidone (125 mL), and $P_2O_5$ (8.8 g, 0.3 eq.) were charged to a round bottom flask. The mixture was heated to a reaction temperature for a reaction time. The reaction mixture was cooled, poured into water, and then cooled to ambient temperature. The precipitated solid was isolated by filtration, washed with water and dried in vacuo at 50° C.

TABLE 4

Reaction times and temperatures for TFA-lysine diketopiperazine synthesis.

| Reaction temp (° C.) | Reaction time | Reaction yield |
|---|---|---|
| 110 | 0.25 | 19% |
| 110 | 5 | 54% |
| 170 | 0.25 | 59% |
| 170 | 5 | 42% |

Example 7

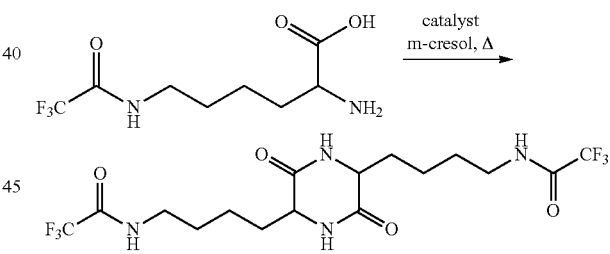

TFA-lysine (10.0 g), m-cresol (22 mL), and $P_2O_5$ were charged to a 250 mL round bottom flask. The mixture was heated to 160-165° C. for 1 hour. The reaction mixture was cooled to 65° C., poured into a solution of 5% aqueous NaOH and methanol, and then cooled to ambient temperature. The precipitated solid was isolated by filtration, washed with water and dried in vacuo at 50° C. Product yield was 12%.

Example 8

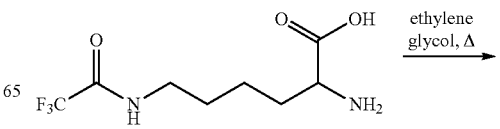

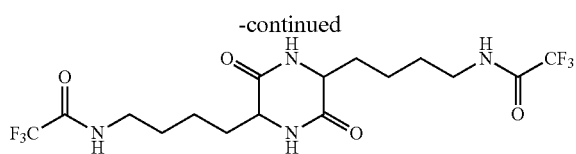

TFA-lysine (50.0 g) and ethylene glycol (150 mL) were charged to a 500 mL round bottom flask. The mixture was heated to 160-170° C. for 2 hours. The reaction mixture was poured into water and cooled to ambient temperature. The precipitated solid was isolated by filtration, washed with water and dried in vacuo at 50° C. Product yield was 2%.

Example 9

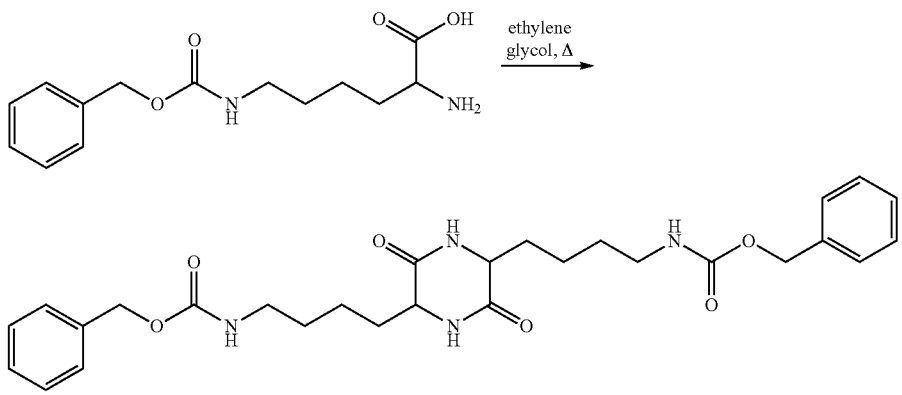

Cbz-lysine (100.0 g) and ethylene glycol (300 mL) were charged to a 1000 mL round bottom flask. The mixture was heated to 160-170° C. for 6 hours. The reaction mixture was poured into a mixture of water and methanol and cooled to ambient temperature. The precipitated solid was isolated by filtration, washed with water and dried in vacuo at 50° C. Product yield was 64%.

Figure 3:
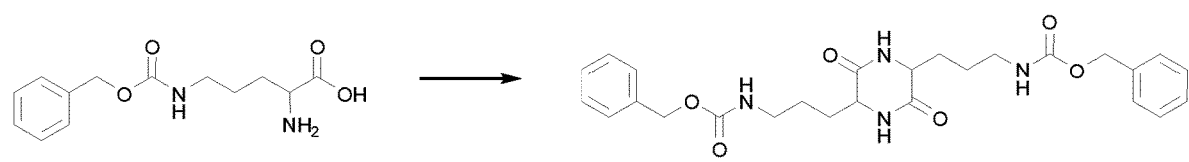
FIG. 3 is a scheme showing the cyclocoondensation of γ-Cbz-ornithine.

FIG. 3 shows a general scheme for the cyclocondensation of γ-Cbz-ornithine.

Example 10

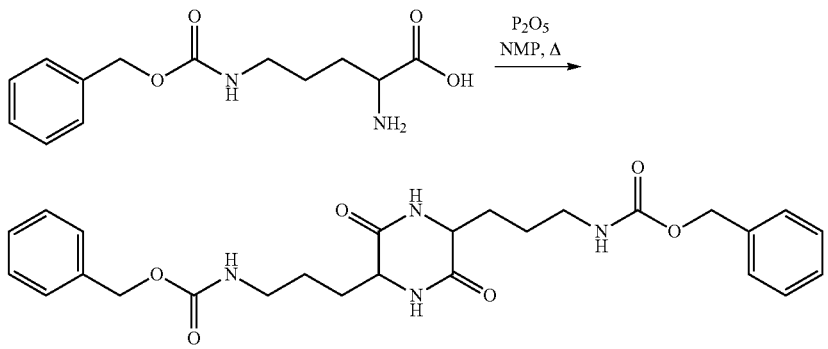

CBz-ornithine (100 g), N-methyl pyrrolidone (194 mL), and $P_2O_5$ (8 g) were charged to a 1000 mL round bottom flask. The mixture was heated to 160-165° C. for 2 hours. The reaction mixture was poured into water and cooled to ambient temperature. The precipitated solid was isolated by filtration, washed with methanol and water, and dried in vacuo at 50° C. The product yield was 51%.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the disclosed embodiments. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosed embodiments are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar references used in the context of describing the disclosed embodiments (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosed embodiments and does not pose a limitation on the scope of the disclosed embodiments unless otherwise claimed. No language in the specification should be construed as indicating any non-claimed element essential to the practice of the disclosed embodiments or any variants thereof.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of any and all Markush groups used in the appended claims.

Preferred embodiments of this invention are described herein, including the best mode known to the inventors for carrying out the invention(s). Of course, variations on the disclosed embodiments will become apparent to those of ordinary skill in the art upon reading the foregoing description. The inventors expect skilled artisans to employ such variations as appropriate, and the inventors intend for the invention(s) to be practiced otherwise than specifically described herein. Accordingly, this disclosure includes all modifications and equivalents of the subject matter recited in the claims appended hereto as permitted by applicable law. Moreover, any combination of the above described elements in all possible variations thereof is encompassed by the disclosed embodiments unless otherwise indicated herein or otherwise clearly contradicted by context.

Furthermore, references have been made to patents and printed publications throughout this specification. Each of the above cited references and printed publications are hereby individually incorporated by reference in their entirety.

Having shown and described an embodiment of the invention, those skilled in the art will realize that many variations and modifications may be made to affect the described invention and still be within the scope of the claimed invention. Additionally, many of the elements indicated above may be altered or replaced by different elements which will provide the same result and fall within the spirit of the claimed invention. It is the intention, therefore, to limit the invention only as indicated by the scope of the claims.

The invention claimed is:

1. A method for the synthesis of a diketopiperazine according to Formula I, the method comprising

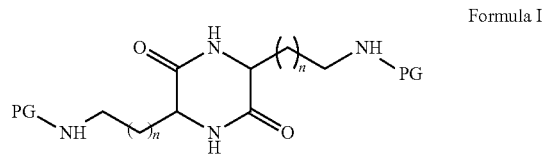

Formula I heating a N-protected amino acid to a temperature of 110° C. to 175° C. in the presence of a catalyst in an organic solvent;
wherein n is 0 to 3;
wherein PG is selected from trifluoroacetyl, CBz, and acetyl;
wherein the catalyst is present in a concentration of 20% to 50% that of the N-protected amino add.

2. The method of claim 1, wherein n is equal to 3.
3. The method of claim 1, wherein PG is trifluoroacetyl.
4. The method of claim 1, wherein PG is Cbz.
5. The method of claim 1, wherein the solvent is N-methyl-2-pyrrolidone.
6. The method of claim 1, wherein the N-protected amino acid is ε-trifluoroacetyl-L-lysine.
7. The method of claim 1, wherein the catalyst is selected from sulfuric acid, phosphoric acid, p-toluenesulfonic acid, 1-propylphosphonic acid cyclic anhydride, tributyl phosphate, phenyl phosphonic acid and phosphorous pentoxide.
8. The method of claim 1, wherein the mixture is heated for between 0.25 and 6 hours.
9. The method of claim 1, wherein the N-protected amino acid is ε-Cbz-L-lysine.
10. The method of claim 1, wherein the N-protected amino acid is γ-trifluoroacetyl-ornithine.
11. The method of claim 1, wherein the N-protected amino acid is γ-Cbz-ornithine.
12. The method of claim 1, wherein the catalyst is phosphorous pentoxide.
13. The method of claim 12, wherein the concentration of phosphorous pentoxide is from 20% to 40% that of the N-protected amino acid.
14. The method of claim 12, wherein the concentration of phosphorous pentoxide is from 20% to 35% that of the N-protected amino acid.
15. The method of claim 1, further comprising the step of quenching the mixture with water.
16. The method of claim 1, wherein the mixture is heated to a temperature of between 130° C. and 175° C.
17. The method of claim 1, wherein the mixture is heated to a temperature of between 150 and 175° C.
18. The method of claim 1, wherein the mixture is heated for between 0.25 and 5 hours.
19. A method for the synthesis of a diketopiperazine according to Formula I, the method comprising:

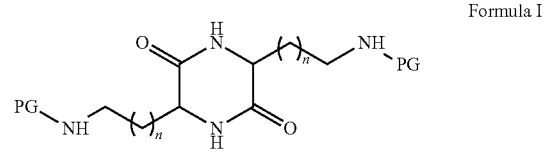

Formula I heating a mixture of an N-protected amino acid of Formula II in the presence of a catalyst in an organic solvent;

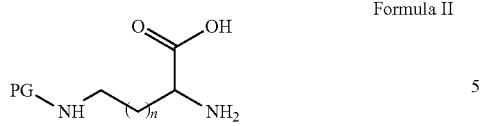

Formula II wherein PG is selected from the group consisting of trifluoroacetyl, CBz, and acetyl, and n is 0 to 3;
wherein the catalyst is phosphorous pentoxide, and is present in a concentration of 20% to 35% that of the amino acid; and
wherein the solvent is selected from the group consisting of: dimethylacetamide, N-methyl-2-pyrrolidone, diglyme, ethyl glyme, proglyme, and ethyldiglyme; and
wherein the mixture is heated to a temperature of between 150° and 175° C. for between 0.25 and 6 hours.

* * * * *